US00PP37409P2

(12) United States Plant Patent
Castorani

(10) Patent No.: US PP37,409 P2
(45) Date of Patent: May 5, 2026

(54) ***GERANIUM* PLANT NAMED 'Dark Roast'**

(50) Latin Name: *Geranium maculatum*
Varietal Denomination: Dark Roast

(71) Applicant: North Creek Nurseries, Hockessin, DE (US)

(72) Inventor: Steven Castorani, Landenberg, PA (US)

(73) Assignee: NORTH CREEK NURSERIES, Hockessin, DE (US)

( * ) Notice: Subject to any disclaimer, the term of this patent is extended or adjusted under 35 U.S.C. 154(b) by 0 days.

(21) Appl. No.: 19/300,753

(22) Filed: Aug. 15, 2025

(51) Int. Cl.
*A01H 5/02* (2018.01)
*A01H 5/12* (2018.01)
*A01H 6/42* (2018.01)

(52) U.S. Cl.
USPC ..... Plt./324

CPC ..... *A01H 6/425* (2018.05); *A01H 5/02* (2013.01); *A01H 5/12* (2013.01)

(58) Field of Classification Search
USPC ..... Plt./324
See application file for complete search history.

(56) References Cited

U.S. PATENT DOCUMENTS

PP36,258 P2 * 11/2024 Horvath ..... A01H 6/42
Plt./324

* cited by examiner

*Primary Examiner* — Susan Mccormick Ewoldt
*Assistant Examiner* — Zachariah Allan Kay
(74) *Attorney, Agent, or Firm* — Penny J. Aguirre

(57) ABSTRACT

A new cultivar of *Geranium maculatum* plant named 'Dark Roast' that is characterized by its flowers that are vibrant fuchsia in color with white throats, its green-burgundy-bronze colored foliage that persists through the summer and into fall with consistent moisture, its palmate-shaped leaves, and its blooming period due to high heat tolerance.

2 Drawing Sheets

Botanical classification: *Geranium maculatum.*
Cultivar designation: 'Dark Roast'.

BACKGROUND OF THE INVENTION

The present invention relates to a new and distinct cultivar of *Geranium* plant, botanically known as *Geranium maculatum* 'Dark Roast' and will be referred to hereafter by its cultivar name, 'Dark Roast'. 'Dark Roast' is a new cultivar of herbaceous perennial grown for use as a garden plant.

'Dark Roast' was discovered by the Inventor as a chance seedling in a garden plot in Landenberg, Pennsylvania in May of 2017. The exact parentage is unknown, however it is most likely a seedling of open pollinated 'Espresso' (not patented) based on its characteristics and its proximity to the new cultivar as the new cultivar was found growing in garden plot of 'Espresso'.

Asexual propagation of the new cultivar was first accomplished by division under the direction of the Inventor in Landenberg, Pennsylvania in April of 2021. Asexual propagation by division and tissue culture tissue using meristematic tissue has determined that the characteristics of the new cultivar are stable and are reproduced true to type in successive generations.

SUMMARY OF THE INVENTION

The following traits have been repeatedly observed and represent the characteristics of 'Dark Roast'. These attributes in combination distinguish 'Dark Roast' as a new and distinct cultivar of *Geranium.*

1. 'Dark Roast' exhibits flowers that are vibrant fuchsia in color with white throats.
2. 'Dark Roast' exhibits green-burgundy-bronze colored foliage that persists through the summer and into fall with consistent moisture.
3. 'Dark Roast' exhibits palmate-shaped leaves.
4. 'Dark Roast' exhibits a long blooming period due to high heat tolerance.

The probable parent plant differs from 'Dark Roast' in having lighter bronze colored foliage that does not last as long in the season, lighter colored flowers and lower heat tolerance. 'Dark Roast' can be most closely compared to the *Geranium* cultivars 'Huggy Bear' (U.S. Plant Pat. No. 36,258) and 'Elizabeth Ann' (U.S. Plant Pat. No. 11,252). 'Huggy Bear' is similar to 'Dark Roast' in having dark green-burgundy-bronze foliage and a long blooming period. 'Huggy Bear' differs from 'Dark Roast' in having flowers that are lighter and less vibrant in color, a less floriferous blooming habit, and foliage that is lighter in color. 'Elizabeth Ann' is similar to 'Dark Roast' in having dark colored foliage, and a similar blooming period. 'Elizabeth Ann' differs from 'Dark Roast' in having flowers that are light pink in color and darker colored foliage.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures includes a website listing by American Beauties Native Plants.

BRIEF DESCRIPTION OF THE DRAWINGS

The accompanying color photographs illustrate the overall appearance and distinct characteristics of the new *Geranium*. The photographs were taken of seven-year-old plants of 'Dark Roast' as grown outdoors in a garden in Hockessin, Delaware.

The photograph in FIG. 1 provides a view of 'Dark Roast' in bloom.

Figure 1:
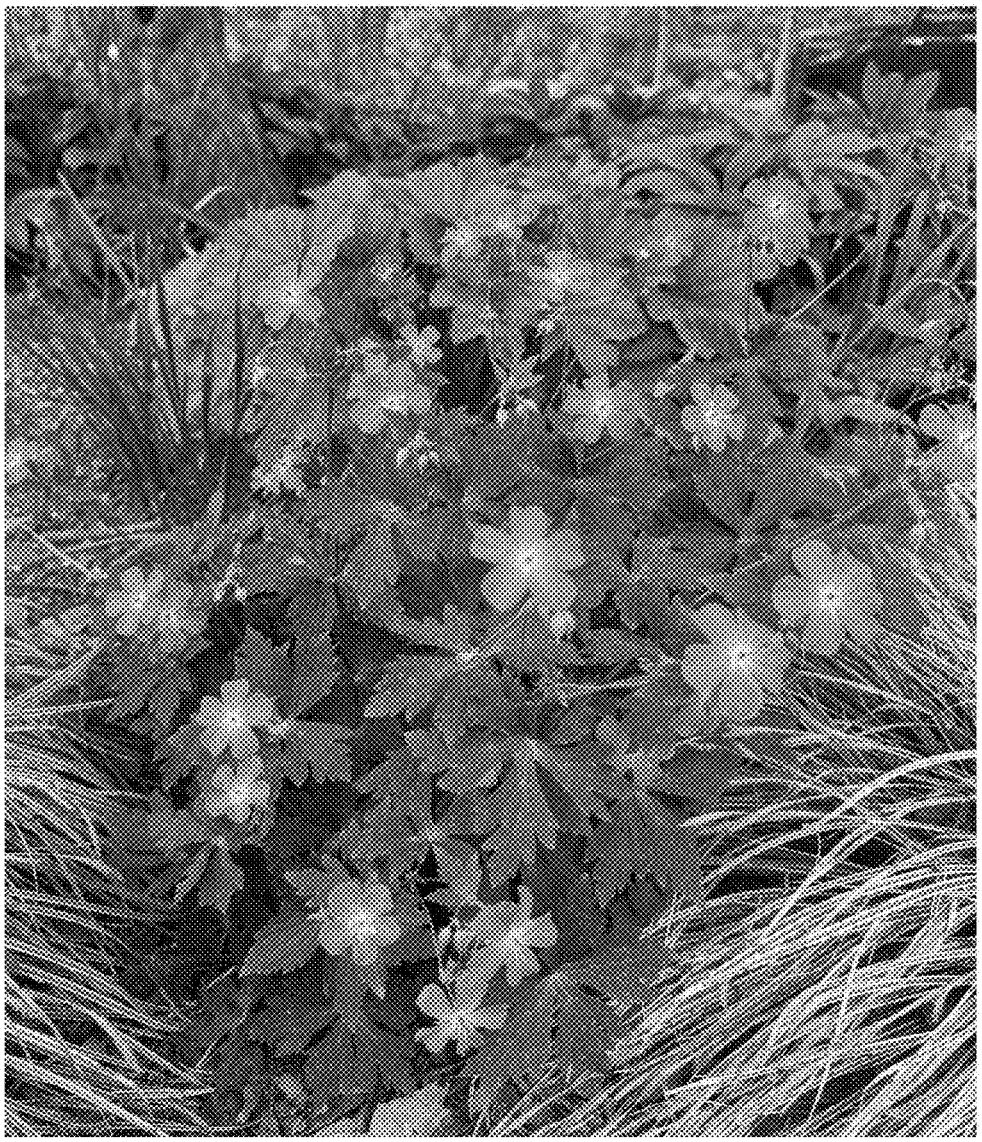
Figure 2:
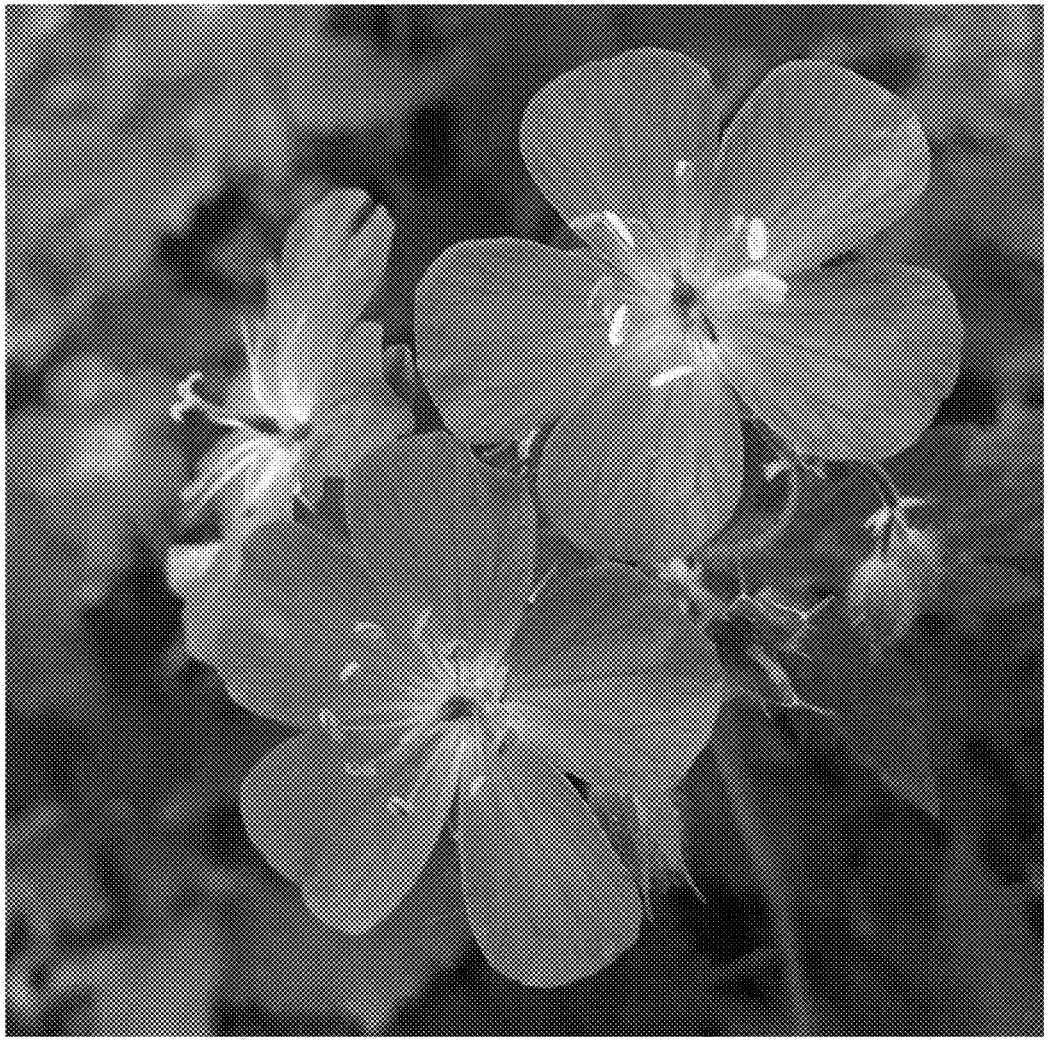

The photograph in FIG. 2 provides a close-up view of the flowers of 'Dark Roast'.

The colors in the photographs are as close as possible with the digital photography and printing techniques utilized and the color codes in the detailed botanical description accurately describe the colors of the new *Geranium*.

DETAILED BOTANICAL DESCRIPTION OF THE PLANT

The following is a detailed description of one year-old plants of the new cultivar as grown in one-gallon containers in Landenberg, Pennsylvania. The phenotype of the new cultivar may vary with variations in environmental, climatic, and cultural conditions, as it has not been tested under all possible environmental conditions. The color determination is in accordance with the 2015 $6^{th}$ edition Colour Chart of The Royal Horticultural Society, London, England, except where general color terms of ordinary dictionary significance are used.

General characteristics:

*Blooming period*.—Mid-April through May 6 to 8 weeks of bloom time.

*Plant type*.—Herbaceous perennial.

*Plant habit*.—Compact mound, broadly spreading.

*Height and spread*.—Average of 13.5 cm in height and 16 cm in spread in the landscape.

*Hardiness*.—At least in U.S.D.A. Zones 4 to 8.

*Diseases and pests*.—No susceptibility or resistance to diseases or pests has been observed.

*Root description*.—Slightly fleshy, 164C in color.

*Root development*.—12 weeks for root initiation from tissue culture, 16 weeks to produce a young rooted plant.

*Propagation*.—Division and tissue culture.

Branch description:

*Branch size*.—Average of 14 cm in length and 2 mm in width.

*Branch shape*.—Round. Branch color — Young; 138B in color, maturing; 138B and N186C.

*Branch surface*.—Slightly glossy, and densely covered with fine and soft tomentose pubescence, average of 3 mm in length, 145C in color.

*Internode length*.—Average of 3 cm.

*Branching habit*.—Freely branched, average of 15 main branches, 35 lateral branches.

Foliage description:

*Leaf shape*.—Reniform (overall shape), palmately cleft with an average of 3 to 5 lobes.

*Leaf division*.—Simple.

*Leaf base*.—Hastate, lobes free to touching.

*Leaf apex*.—Acute.

*Leaf venation*.—Palmate, upper surface; mostly inconspicuous, center to mid-center 145A in color, lower surface; 138A.

*Leaf margins*.—Lanciniate.

*Leaf aspect*.—Outward to drooping.

*Leaf lobes*.—Sinuses are deep to moderately deep, sinus orientation is convergent.

*Leaf attachment*.—Petiolate.

*Leaf arrangement*.—Opposite.

*Leaf surface*.—Both surfaces rugose, moderately glossy, upper and lower surface; covered with soft short pubescence; an average of 0.5 mm in length, 138A to NN137A in color, lower main vein densely covered 138A in color, fine hairs, 0.5 mm in length.

*Leaf color*.—Young upper and lower surface; a blend of 150A and 148A, mature upper surface; N138A, turning to a blend of N186A and N186C, mature lower surface; N186B and NN137A.

*Leaf size*.—Average of 5 cm in length, 4.5 cm in width.

*Leaf quantity*.—Average of 8 (4 pairs) per lateral branch.

*Petioles*.—Average of 2 cm in length and 2 mm in width, color; a blend of NN137A and N186B, both surfaces are slightly glossy, densely covered with short hairs an average of 1 mm in length and N155A.

*Stipules*.—2 leafy stipules, present at the base of the leaves, linear in shape, apex is acute, base cuneate, average of 3 mm in length, 1 mm in width, 144B in color.

Flower description:

*Inflorescence type*.—Axillary, solitary.

*Lastingness of flowers*.—Average of 7 days, self cleaning.

*Flowers*.—Average of 25 per plant, rotate, single, average of 5 cm and diameter, 1 cm in depth, primarily facing upward to outward.

*Flower fragrance*.—None.

*Flower bud*.—An average of 1.5 cm in length, 8 mm in width, color; a blend of 138A and 144B, tips NN137A, ovate in shape, surface is sparsely covered with fine soft tomentose pubescent hairs 5 mm in length, and a blend of 157A in color.

*Petals*.—5, rotate in arrangement, 1 whorl, obcordate in shape, narrow cuneate base, broadly retuse apex, entire margins, slightly undulate, surfaces are glabrous, velvety, and matte, average of 2.5 cm in length, 2 cm in width, color: when opening upper surface; 75A and 75B, when opening lower surface; 75C, base 145C, veined N75B, when fully open upper and lower surface; N87A and N80A, base N155D, veins 94A.

*Calyx*.—Rotate, average of 5 mm in depth and 1.7 cm in width.

*Sepals*.—Average of 5, linear in shape, entire margins that are slightly translucent, mucronate apex, cuneate base, average of 1.3 cm length, 4 mm in width, color of both surfaces 145B, upper surface is glabrous and slightly glossy, lower surface is glabrous, matte and densely covered with short hairs 1 mm in length, matches surface color to NN155D.

*Peduncles*.—Average of 8 cm in length and 1.5 mm in diameter, held in an upright to nodding angle, 143B to N186B in color, surfaces are matte, surfaces covered in pubescence; on mature peduncles, 138A in color, canescent pubescence, 0.5 mm in length, pubescence on young peduncles is very dense hirsute pubescence, NN155D, 1 mm in length.

*Pedicels*.—Average of 3 cm in length and 1.5 mm in diameter, held in a 90° angle to the penducle, 143B in color, surfaces are matte, surfaces covered in hirsute pubescence.

*Floral bracts*.—None.

Reproductive organs:

*Gynoecium*.—Pistil; 1, average of 8 mm in length, stigmas; 5, flattened and star-shaped, 2 mm in length, 1 mm in diameter, 176A in color, style; slightly glossy surface, average of 6 mm in length, color; 183A, base 200B, ovary; oval, superior, 143B in color.

*Androecium*.—Stamens; 10, anthers; dorsifixed, narrow oblong in shape,, 2.2 mm in length, 0.5 mm in width, young color 161A in color, mature color 203A, filaments; 1.3 cm in length, color; N81A, base 144C, pollen; high in quantity, 158D in color.

*Fruit/seeds*.—No fruit or seeds have been observed to date.

It is claimed:

1. A new and distinct cultivar of *Geranium* plant named 'Dark Roast' as herein illustrated and described.

* * * * *